(12) United States Patent  
Kim et al.

(10) Patent No.: US 8,666,431 B2
(45) Date of Patent: Mar. 4, 2014

(54) WATER-QUALITY MEASUREMENT SYSTEM USING A SMARTPHONE

(75) Inventors: Hyunook Kim, Seoul (KR); Young Min Hong, Uijeongbu (KR); Jun Kuk Kang, Gunpo (KR); Dong Chul Kang, Anyang (KR); Chang Yong Oh, Seoul (KR)

(73) Assignees: NDS Corporation (KR); Hyunook Kim (KR)

( * ) Notice: Subject to any disclaimer, the term of this patent is extended or adjusted under 35 U.S.C. 154(b) by 0 days.

(21) Appl. No.: 13/510,490

(22) PCT Filed: Mar. 30, 2011

(86) PCT No.: PCT/KR2011/002182
§ 371 (c)(1),
(2), (4) Date: May 17, 2012

(87) PCT Pub. No.: WO2011/132863
PCT Pub. Date: Oct. 27, 2011

(65) Prior Publication Data
US 2013/0029683 A1    Jan. 31, 2013

(30) Foreign Application Priority Data

Apr. 19, 2010  (KR) .................. 10-2010-0035776
Jun. 28, 2010  (KR) .................. 10-2010-0060977

(51) Int. Cl.
*H04W 24/00*    (2009.01)
(52) U.S. Cl.
USPC ................. 455/456.1; 455/66.1; 455/11.1
(58) Field of Classification Search
USPC ........ 455/456.1, 11.1; 340/340, 870.07, 10.4, 340/10.3, 10.1, 604, 540, 628
See application file for complete search history.

(56) References Cited

U.S. PATENT DOCUMENTS

| | | | |
|---|---|---|---|
| 7,424,399 B2 * | 9/2008 | Kahn et al. ................... | 702/188 |
| 2007/0050157 A1* | 3/2007 | Kahn et al. ................... | 702/55 |
| 2007/0219728 A1* | 9/2007 | Papageorgiou et al. ........ | 702/23 |
| 2008/0109175 A1* | 5/2008 | Michalak ....................... | 702/50 |
| 2010/0085211 A1* | 4/2010 | Wang et al. ............... | 340/870.02 |
| 2010/0206039 A1* | 8/2010 | Kates ........................... | 73/1.01 |
| 2010/0271217 A1* | 10/2010 | Kates ........................... | 340/604 |
| 2011/0307203 A1* | 12/2011 | Higgins et al. ................. | 702/84 |
| 2011/0307221 A1* | 12/2011 | Higgins et al. ................ | 702/187 |

FOREIGN PATENT DOCUMENTS

| | | |
|---|---|---|
| KR | 1020020005881 | 1/2002 |
| KR | 200369054 | 11/2004 |
| KR | 1020060109543 | 10/2006 |
| KR | 1020090097296 | 9/2009 |

OTHER PUBLICATIONS

International Search report—PCT/KR2011/002182 dated Nov. 28, 2011.

* cited by examiner

*Primary Examiner* — Joseph Arevalo
(74) *Attorney, Agent, or Firm* — Cantor Colburn LLP

(57) ABSTRACT

This invention relates to a system for measuring water quality using a smartphone, and more particularly to a system for measuring water quality using a smartphone, in which, to solve problems of hand-operated and manual water quality measurement methods and in order to increase reliability and accuracy, a water quality meter and a smartphone, which mutually communicate with each other, are utilized, and also, the smartphone is provided with a memory unit, a calculation unit, a GPS unit, etc., thus enabling water quality to be measured in real time and water quality data to be stored and transferred to the outside, so that reliability and accuracy of the measured water quality data may be improved.

1 Claim, 1 Drawing Sheet

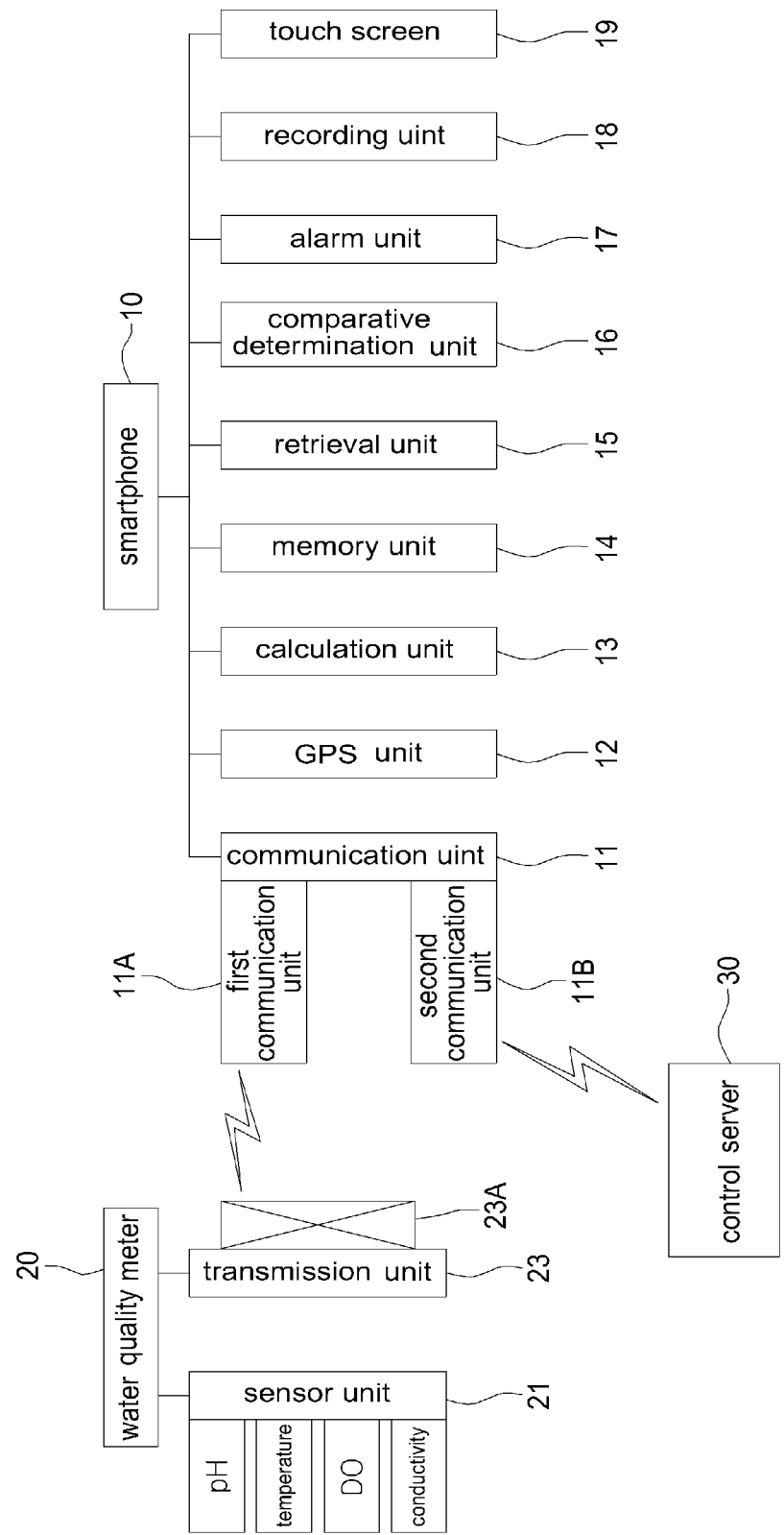

WATER-QUALITY MEASUREMENT SYSTEM USING A SMARTPHONE

TECHNICAL FIELD

The present invention relates to a system for measuring water quality using a smartphone, and more particularly to a system for measuring water quality using a smartphone, in which, to solve problems of hand-operated and manual water quality measurement methods and in order to increase reliability and accuracy, a water quality meter and a smartphone, which mutually communicate with each other, are utilized, and also the smartphone is provided with a memory unit, a calculation unit, a GPS (Global Positioning System) unit, etc., thus enabling water quality to be measured in real time and water quality data to be stored and transferred to the outside, so that reliability and accuracy of the measured water quality data may be improved.

BACKGROUND ART

In order to measure water quality according to the Enforcement Decree Of The Water Quality And Ecosystem Conservation Act and the Enforcement Decree Of The Soil Environment Conservation Act as well as the Water Quality Pollution Process Test Standards which are based on Environment Notification, an inspector primarily measures the pH, temperature, DO (Dissolved Oxygen), electrical conductivity, etc., at sites such as rivers or the like using a water quality measuring instrument and manually records them, and secondarily gathers a sample to transfer it to an authorized inspection office. In this procedure, there are problems of a drop in reliability and accuracy because of the inaccuracy of the position at which the sample is gathered and the manual recording of initial water quality data and also problems of reliability not being guaranteed due to mistakes in recording or the probability of fabricating data. Furthermore, because data should be put in order after having surveyed many sites at which water quality is to be measured, there are the problems of complication and time consumption, which must be solved.

Korean Unexamined Patent Application Publication No. 2009-0097296 (Sep. 16, 2009) by NDS Corporation as the applicant of the present invention discloses an apparatus for measuring water quality and a communication method thereof. In the communication method between a conventional apparatus for measuring water quality and a control server, because the apparatus may communicate with the control server using a communication method selected upon manufacture, the case where the apparatus is installed in the region where the communication method that was selected is not supported makes it impossible to execute communication with the control server. In order to solve this problem, the above patent proposes a technique that is able to communicate with the control server regardless of the installation location by supporting a variety of communication methods so that these methods may be used.

The present invention is devised to use the technique of the above patent in order to solve problems of inefficiency and unreliability that are caused by conventional water quality measurement methods performed in accordance with the Water Quality Pollution Process Test Standards.

DISCLOSURE

Technical Problem

Accordingly, an object of the present invention is to provide a system for measuring water quality, which adopts a smartphone which has recently been receiving attention and in which the application fields thereof are widened, thus increasing reliability and accuracy and drastically reducing the data arrangement time to thereby greatly increase work efficiency.

More specifically, an object of the present invention is to provide a system for measuring water quality, which includes a water quality meter and a smartphone which may execute wired/wireless communication with the water quality meter, and the smartphone is provided with a calculation unit for calculating data obtained using the water quality meter and a GPS unit, and water quality data stored in a memory unit may be transferred to a control center or concerned agencies along with GPS information so as to impart reliability and accuracy to the water quality data for sites such as rivers or the like.

Another object of the present invention is to provide a system for measuring water quality, in which the smartphone is further provided with a retrieval unit for retrieving water quality data stored in the memory unit, a comparative determination unit for comparing the standard with the measured water quality data stored in the memory unit, an alarm unit for providing a water quality pollution alarm when the comparative determination unit determines that the measured water quality data is greater than the standard, and a recording unit for recording a water quality measurement diary, thus greatly increasing the convenience, accuracy and efficiency of use of the data.

Technical Solution

In order to accomplish the above object, the present invention provides a system for measuring water quality, including a water quality meter having a sensor unit and a transmission unit; and a smartphone, including a first communication unit corresponding to the transmission unit of the water quality meter, a calculation unit for calculating data obtained using the water quality meter, a GPS unit, a memory unit in which a processing program for the calculation unit is stored and which stores water quality data processed by the calculation unit and GPS information of the GPS unit, and a second communication unit for sending the water quality data and the GPS information stored in the memory unit to the outside.

In this system, the smartphone may further include a retrieval unit for retrieving the water quality data stored in the memory unit.

In this system, a water quality standard may be stored in the memory unit, and the smartphone may further include a comparative determination unit for comparing the standard with the measured water quality data, and an alarm unit for providing a water quality pollution alarm when the comparative determination unit determines that the measured water quality data is greater than the standard.

The smartphone may further include a recording unit for recording a water quality measurement diary, and the diary of the recording unit is preferably stored in the memory unit.

Advantageous Effects

According to the present invention, a system for measuring water quality includes a water quality meter and a smartphone which enables wired/wireless communication with the water quality meter. The smartphone includes a calculation unit for calculating data obtained using the water quality meter and a GPS unit. Also, water quality data stored in a memory unit can be transferred to a control center or concerned agencies along with GPS information so as to impart reliability and accuracy to the water quality data for sites such as rivers or the like.

Also, the smartphone is further provided with a retrieval unit for retrieving water quality data stored in the memory unit, a comparative determination unit for comparing the standard with the measured water quality data stored in the memory unit, an alarm unit for providing a water quality pollution alarm when the comparative determination unit determines that the measured water quality data is greater than the standard, and a recording unit for recording a water quality measurement diary, thus greatly increasing convenience, accuracy and efficiency of use of the data. Consequently, water quality can be measured using the smartphone which has recently been receiving attention and in which the application fields thereof are widened, thus increasing reliability and accuracy and drastically reducing the data arrangement time to thereby greatly increase work efficiency.

DESCRIPTION OF DRAWING

FIG. 1 is a block diagram illustrating a system for measuring water quality according to the present invention.

<Description of the Reference Numerals in the Drawing>

| | |
|---|---|
| 10: smartphone | 11: communication unit |
| 12: GPS unit | 13: calculation unit |
| 14: memory unit | 15: retrieval unit |
| 16: comparative determination unit | |
| 17: alarm unit | 17: recording unit |
| 20: water quality meter | 21: sensor unit |
| 23: transmission unit | 30: control server |

MODE FOR INVENTION

Hereinafter, the invention will now be described more fully hereinafter with reference to the accompanying drawing.

This invention may be variously modified and embodied in many different forms, and embodiments (or aspects) are to be specifically described therein. However, this invention should not be construed as limited to specific disclosure forms, and the spirit and scope of the invention should be understood as incorporating various modifications, additions and substitutions.

Wherever possible, the same reference numerals, in particular, the reference numerals in which a two-digit number and one-digit number are the same or a two-digit number, one-digit number and letters of the alphabet are the same, will be used throughout the drawings and the description to refer to the same or like members. Unless otherwise stated, the members designated by respective reference numerals in the drawings are regarded as members based on such standards.

The terminology used herein is for the purpose of describing particular embodiments only and is not intended to be limiting. As used herein, the singular forms are intended to include the plural forms as well, unless the context clearly indicates otherwise. It will be further understood that the terms "comprises" and/or "comprising," or "includes" and/or "including" when used in this specification, specify the presence of stated features, numbers, steps, operations, elements, components or combinations thereof, but do not preclude the presence or addition of one or more other features, numbers, steps, operations, elements, components or combinations thereof.

Unless otherwise defined, all terms used herein, including technical or scientific terms, have the same meanings as those generally understood by those with ordinary knowledge in the field of the art to which the present invention belongs. Such terms as those defined in generally used dictionaries and are to be interpreted as having meanings equivalent to the contextual meanings in the relevant field of art, and are not to be interpreted as having ideal or excessively formal meanings unless clearly defined as having such in the present application.

It will be understood that the terms first, second, etc. may be used herein to describe different elements, and the sequence of formation thereof does not matter. These terms may be differently described in the detailed description and the claims of the invention.

As illustrated in FIG. 1, the system for measuring water quality according to the present invention includes a smartphone 10, a water quality meter 20, and a control server 30.

The smartphone 10 is exemplified by an i-phone, which is provided with a variety of operating systems (OS) and is able to be installed with additional programs depending on the user's needs, and for which applied programs for example applications are being variously developed.

The system for measuring water quality according to the present invention increases the convenience and reliability of water quality measurement and data arrangement by introducing applied programs which are compatible with the water quality meter into the smartphone.

The water quality meter 20 which communicates with the smartphone 10 is used to measure water quality according to the Enforcement Decree Of The Water Quality And Ecosystem Conservation Act and the Enforcement Decree Of The Soil Environment Conservation Act as well as the Water Quality Pollution Process Test Standards which are based on Environment Notification, thus ensuring reliability, accuracy and convenience in terms of primarily measuring the pH, temperature, DO, electrical conductivity, etc., at sites such as rivers or the like by an inspector.

A sensor unit 21 of the water quality meter 20 may include a sensor for measuring water quality data such as the pH, temperature, DO and electrical conductivity, and as well a variety of additional sensors, if necessary.

A transmission unit 23 of the water quality meter 20 transmits the sensed water quality data to a first communication unit of the smartphone 10, and also may be modified to enable both transmission and reception depending on the introduced functions. Hence, this transmission unit does not exclude the concept of the reception unit.

A communication unit 11 (in particular, a first communication unit 11A) of the smartphone 10 and the transmission unit 23 of the water quality meter 20 may communicate with each other using wired or wireless communication (in particular bluetooth communication). To this end, a known wired/wireless communication conversion unit 23A is preferably provided.

As disclosed in Korean Unexamined Patent Application Publication No. 2009-0097296, a variety of communication modules may be introduced to carry out communication between the communication unit 11 (in particular a second communication unit 11B) of the smartphone 10 and the control server 30 or between the smartphone 10 and the water quality meter 20.

In order to construct an applied program system, the smartphone 10 includes the first communication unit 11A corresponding to the transmission unit 23 of the water quality meter 20, a calculation unit 13 for calculating the data obtained using the water quality meter 20, a GPS unit 12, a memory unit 14 in which a processing program for the calculation unit is stored and which stores water quality data processed by the calculation unit and GPS information of the GPS unit, and the second communication unit 11B for sending the water quality data and the GPS information stored in the memory unit to the outside, in particular, the control server 30.

The GPS unit 12 is used to accurately and reliably record position information of the sites such as rivers or the like surveyed by an inspector, so that accuracy is imparted to the primary water quality data including the pH, temperature, DO, electrical conductivity, etc., and the secondary water quality data at the inspection office using sampling. Both the water quality data and the position information are recorded in the control server, and water quality of respective sites may be recorded on the condition board, if necessary, thus systematically and overall managing and controlling the water quality in real time.

Also to enhance the function of managing water quality in real time, a water quality standard is stored in the memory unit 14, and the smartphone preferably further includes a comparative determination unit 16 for comparing the standard with the measured water quality data, and an alarm unit 17 for providing a water quality pollution alarm when the comparative determination unit determines that the measured water quality data is greater than the standard.

The alarm unit 17 may be for example an SMS text message sending unit, and the corresponding alarm text message may be transmitted to mobile phones of person(s) who manage the water quality including the control server.

In the system for measuring water quality according to the present invention, the smartphone preferably further includes a retrieval unit 15 for retrieving the water quality data stored in the memory unit 14, and the retrieval may be implemented using a touch input unit or a keypad provided to the display.

The smartphone preferably further includes a recording unit 18 for recording various work histories including water quality measurement diaries or a variety of memos.

Although typically known techniques related to the operating systems, applied programs and the other functions of the smartphone or related to the water quality meter have been omitted, they may be easily anticipated, deduced and reproduced by those skilled in the art.

Although a preferred embodiment of the present invention regarding the system for measuring water quality having specific shape and configuration with reference to the drawing has been described for illustrative purposes, those skilled in the art will appreciate that various modifications, additions and substitutions are possible, without departing from the scope and spirit of the invention as disclosed in the accompanying claims.

The invention claimed is:

1. A system for measuring water quality, comprising:
a water quality meter having a sensor unit and a transmission unit, wherein the sensor unit includes a sensor for measuring water quality data, and the water quality data includes a potential hydrogen ("pH"), a temperature, a dissolved oxygen ("DO") and an electrical conductivity; and
a smartphone, comprising:
a first communication unit corresponding to the transmission unit of the water quality meter,
a calculation unit for calculating data obtained using the water quality meter,
a GPS (Global Positioning System) unit,
a memory unit in which a processing program for the calculation unit is stored and which stores water quality data processed by the calculation unit and GPS information of the GPS unit, a water quality standard being stored in the memory unit,
a second communication unit for sending the water quality data and the GPS information stored in the memory unit to outside,
a retrieval unit for retrieving the water quality data stored in the memory unit,
a comparative determination unit for comparing the water quality standard with the measured water quality data,
an alarm unit for providing a water quality pollution alarm when the comparative determination unit determines that the measured water quality data is greater than the water quality standard, and
a recording unit for recording a water quality measurement diary, the water quality measurement diary of the recording unit being stored in the memory unit.

* * * * *